(12) United States Patent
Pozzato

(10) Patent No.: US 8,457,751 B2
(45) Date of Patent: Jun. 4, 2013

(54) DEVICE FOR TREATING SKIN AGEING

(75) Inventor: Gianantonio Pozzato, Vicenza (IT)

(73) Assignee: Telea Electronic Engineering S.r.l., Sandrigo (VI) (IT)

( * ) Notice: Subject to any disclaimer, the term of this patent is extended or adjusted under 35 U.S.C. 154(b) by 845 days.

(21) Appl. No.: 12/489,186

(22) Filed: Jun. 22, 2009

(65) Prior Publication Data

US 2010/0010481 A1    Jan. 14, 2010

Related U.S. Application Data

(63) Continuation of application No. 10/520,264, filed on Jan. 6, 2005, now Pat. No. 7,571,003.

(30) Foreign Application Priority Data

Jun. 6, 2003 (IT) ................ VI2003A0110
Jun. 6, 2003 (IT) ................ VI2003A0111

(51) Int. Cl.
*A61N 1/18* (2006.01)
*A61N 1/32* (2006.01)

(52) U.S. Cl.
CPC ......... *A61N 1/328* (2013.01); *A61N 1/326* (2013.01)
USPC .................................................. 607/50

(58) Field of Classification Search
CPC ................................................... A61N 1/328
USPC ............................................ 607/50
See application file for complete search history.

(56) References Cited

U.S. PATENT DOCUMENTS

| 2,311,935 | A | | 2/1943 | Dobert |
| 3,851,651 | A | | 12/1974 | Icenbice, Jr. |
| 4,312,340 | A | * | 1/1982 | Donadelli ............... 604/20 |
| 5,058,605 | A | | 10/1991 | Slovak |
| 6,142,972 | A | | 11/2000 | Cheikh |
| 6,463,336 | B1 | * | 10/2002 | Mawhinney ............ 607/156 |
| 6,684,106 | B2 | | 1/2004 | Herbst |
| 6,882,884 | B1 | | 4/2005 | Mosk et al. |
| 7,571,003 | B2 | * | 8/2009 | Pozzato ................ 607/50 |
| 2004/0049229 | A1 | * | 3/2004 | Taricco ............... 607/1 |

FOREIGN PATENT DOCUMENTS

| FR | 2394301 A1 | 1/1979 |
| FR | 2753385 A1 | 3/1998 |

* cited by examiner

*Primary Examiner* — Joseph Stoklosa
(74) *Attorney, Agent, or Firm* — IP Strategies

(57) ABSTRACT

A device for carrying out a cosmetic method or treating skin ageing and the method comprising the following steps: a) connecting an electronic device, able to generate high frequency electric current waves having a distorted sinusoidal wave form by the presence of harmonics, to one or more electrodes of essentially laminar shape; b) applying said one or more electrodes on the skin surface in the area to be treated; c) activating said electronic device in order to transfer said current waves to said one or more electrodes and to maintain said device activated for a predetermined time; d) deactivating said device and removing the electrodes from the contact with the treated area.

15 Claims, 2 Drawing Sheets

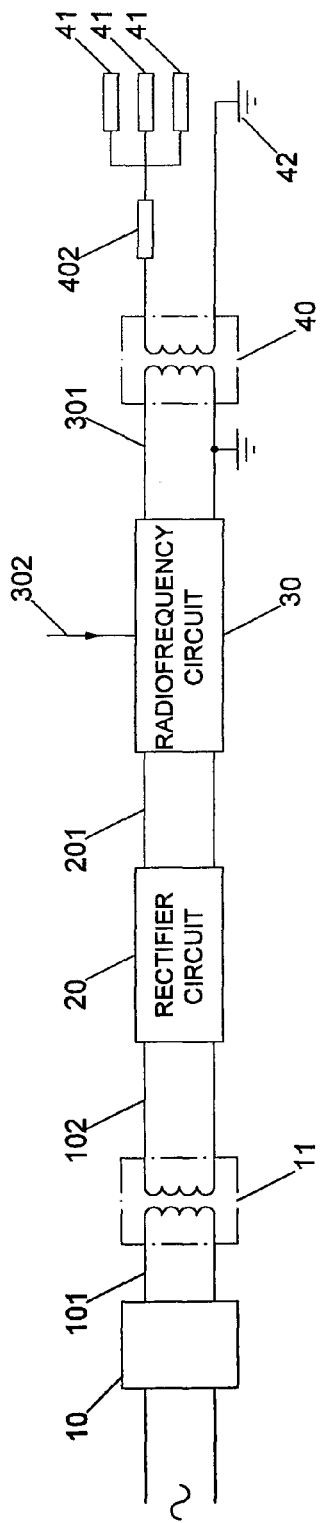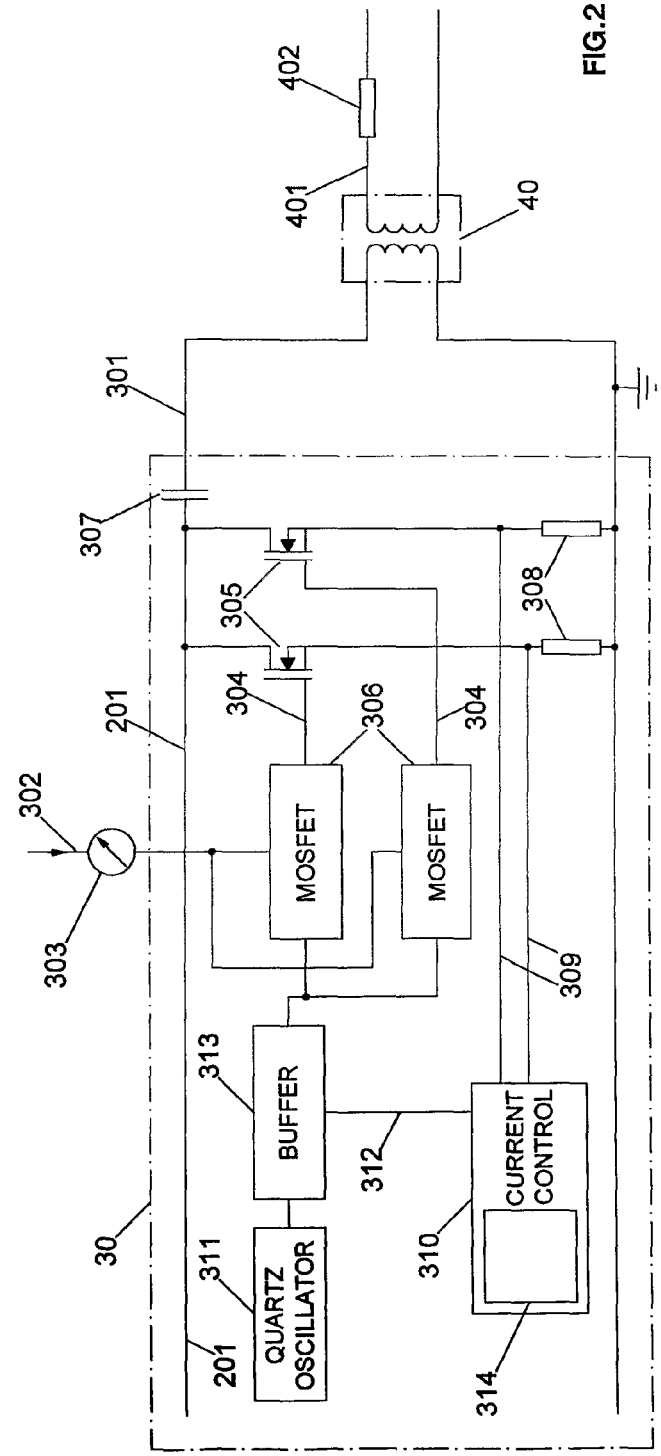

DEVICE FOR TREATING SKIN AGEING

FIELD OF THE INVENTION

The invention relates to a cosmetic method of treating skin ageing and a device for carrying out said method.

BACKGROUND OF THE INVENTION

As from the ancient times, the cosmetic art was interested in somehow treating ageing effects, especially on the skin, in order to reduce as far as possible the unpleasant aesthetical effects that ageing causes in the aspect of persons with the appearance of wrinkles and skin and muscular tissue relaxation.

Even if some means for fighting against skin ageing have changed over the centuries, it can be essentially stated that the main treatments still used today are related to skin treatment by the application of creams on the skin combined with a massage, in order to make absorption easier.

Cosmetic creams have active principles, sometimes natural and sometimes obtained with chemical synthesis, which mainly act on the superficial layer of the skin in order to limit or to eliminate the wrinkled quality acquired by the skin with the passing of time.

Generally, a skin recovery cosmetic functionally acts on the hydration of either deep or superficial layers of the skin, reducing as far as possible the loss of water in the cells and thus restoring the turgidity of the skin.

Another action exerted by actual cosmetic products is to reduce the thickness of the more external (horny layer) of the skin, restoring in it a certain elasticity. There are also cosmetic treatments directed to reduce excess free radicals which, if present in the skin, begin to destroy the membranes of the more superficial cells of the skin, which are the main defense against the external environment.

Cosmetic and medical treatments are user to reduce the effect of free radicals, also in function of the effects they have on the more external tissues, that is, the skin.

One of the limits of the aforesaid cosmetic treatments is the fact that such treatment substantially involves the superficial layer of the skin, and it does not eliminate the causes of ageing.

Consequently, said treatments have to be repeated over time and they are not suitable for providing stable results.

SUMMARY OF THE INVENTION

It is the main object of the invention to provide for a cosmetic method of treating skin ageing that gives stable results over time and which is without unwelcome effects.

It is another object of the invention to provide for a cosmetic method that eliminates in a substantially definitive way ageing effects, such as both the formation of wrinkles on the skin and relaxation of the skin and its support tissues.

It is a further object of the invention to provide for a cosmetic method that is easy to use and does not have any collateral or unwelcome effect on the organism on which the treatment is being applied.

Not the least object is the possibility of performing a treatment using a device that is efficient and inexpensive.

The above-mentioned objects, and others which will be better highlighted in the following description, are attained by a cosmetic method of treating skin ageing characterized by the following steps:
 a) connecting an electronic device able to generate high frequency electric current waves, having a distorted sinusoidal wave form by the presence of harmonics, to one or more electrodes of essentially laminar shape;
 b) applying said one or more electrodes on the skin surface in the area to be treated;
 c) activating said electronic device in order to transfer said current waves to said one or more electrodes and to maintain said device activated for a predetermined time; and
 d) deactivating said device and removing the electrodes from the contact with the treated area.

It is also an aspect of the present invention to provide the device carrying out the aforesaid method and essentially comprising one or more electrodes of essentially laminar shape, to be applied on the skin by adherence and connected to an electronic device, said electronic device comprising:
 a rectifier circuit fed by power grid voltage that supplies a direct voltage, preferably stabilized, to a radiofrequency circuit;
 a radiofrequency circuit comprising at least an electronic switch fed by said voltage and piloted by a piloting circuit,
characterized in that said radiofrequency circuit output consists of a current wave of distorted sinusoidal form by the presence of harmonics of at least the second and third order, said current wave circulating in a broadband resonant circuit on the frequency of the pure wave of said distorted sinusoidal form.

Advantageously, according to the method of the invention, one or more essentially laminar electrodes are applied on the parts of the skin areas that have to be treated against ageing, in order to follow without difficulties the shape of the skin surface.

In a preferred embodiment of the invention, the electrodes are also provided with an adhesive substance that helps maintenance of the contact on the skin during the application of the waveform generated by the electronic device.

The electronic device carrying out the method of the invention is a device in which the resultant wave applied to the electrodes is a wave preferably having a main frequency of 4 MHz and having harmonics of second, third and fourth order.

The effect of the application of such waveforms directly on the skin is to operate in the muscular layers disposed beneath the epidermis, which is the outermost tissue of the skin, so that cellular regeneration action is stimulated.

From performed tests it was recognized that cellular regeneration is also matched with permeability recovery of the cell wall, which becomes impermeable with ageing and has included therein fats and harmful substances for the same cell's life.

The regeneration possibility of the muscle beneath the skin, and thus muscular tone recovery, allows a stable increase of said muscle volume and therefore the consequent stretching of the overlying skin, so that the wrinkled quality and relaxation effects, typical of ageing of the skin and its muscle below, disappear.

BRIEF DESCRIPTION OF THE DRAWINGS

Further characteristics and advantages of the invention will be better highlighted in a particular preferred embodiment of the invention, provided in an explanatory but not limiting way, with references to the figures of the annexed drawings, wherein:

FIG. 1 shows a flow chart of the electronic device of the invention:

FIG. 2 shows in detail the radiofrequency circuit belonging to the electronic device of FIG. 1.

DETAILED DESCRIPTION OF THE INVENTION

Figure 3:
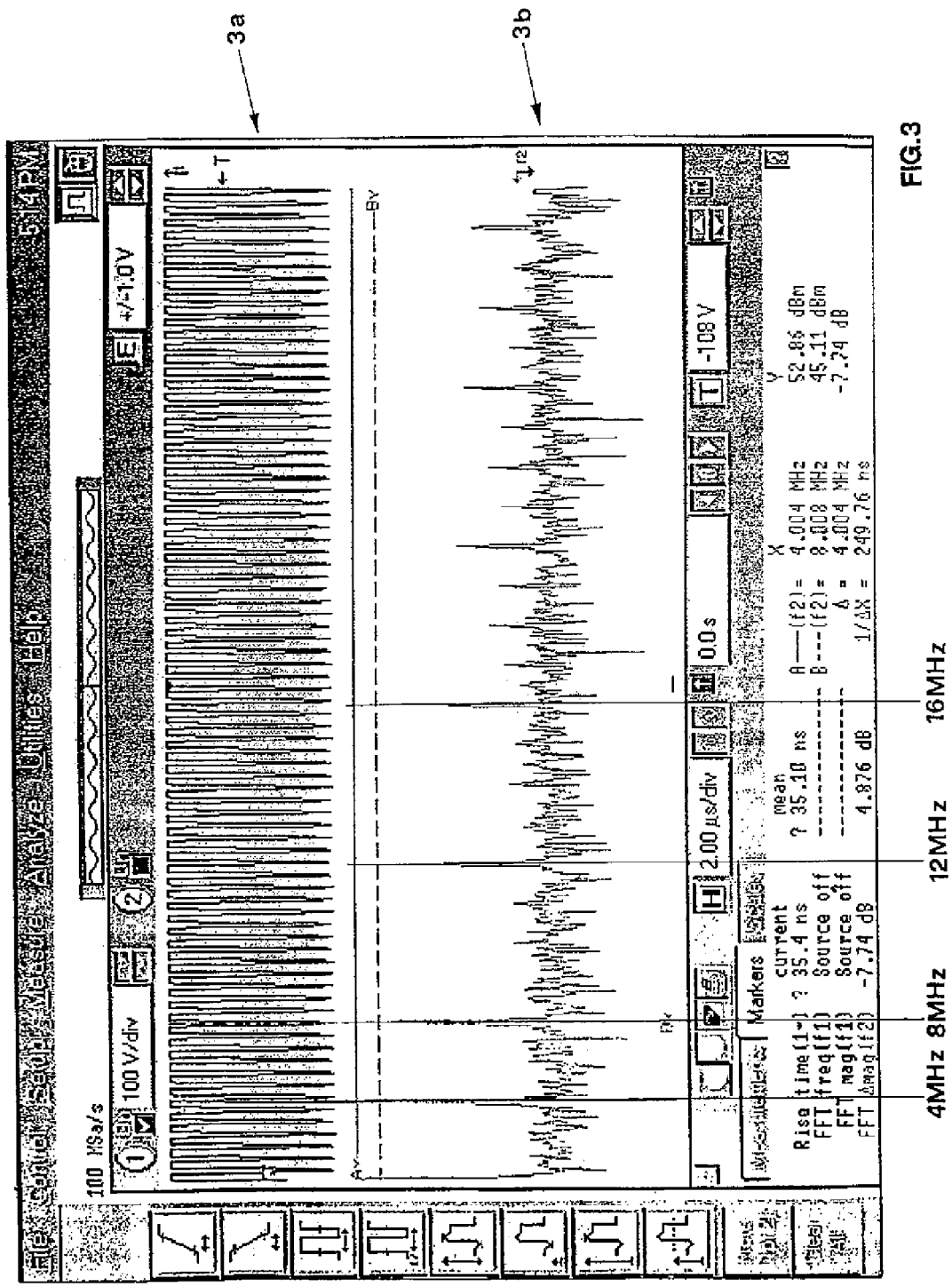
FIG. 3 shows the wave form, with reference to the different frequencies, of the available power at the electrodes of the electronic device of the invention.

With reference to the aforesaid figures, in particular to FIG. 1, it is noted that the circuit carrying out the electronic device is fed by power grid voltage, and it is provided with an input filter 10 for protection against possible radiofrequency interference, present in the power grid or capable of being transferred from the power grid to the electronic device.

The circuit is then provided with a transformer, indicated with numeral 11, to which a voltage 101, for instance of 230V, is applied and a reduced voltage 102, of about 140 or 160V, is provided. Said voltage enters the rectifier circuit 20, which is a common double half-wave diode rectifier circuit in the example, transforming the alternating current into a pulsing rectified current, which is then filtered in order to have a rather high direct voltage 201 as an output, for instance of 220V, which is the radiofrequency circuit 30 supply.

According to a preferred embodiment of the invention, instead of the transformer 11 and the rectifier with filter 20, a stabilized switching AC/DC converter can be used, or transformer coupled with a rectifier with filter having a stabilized switching DC/DC converter output.

These solutions, for the technician expert in the related field, are not shown. In any case, the voltage 201 provided by these rectifiers should be direct and rectified, with a pre-set value preferably in a range, for instance, between 50V and 200V, where the chosen voltage value depends on the utilization of the device.

Said radiofrequency circuit is better shown in FIG. 2.

In the embodiment of the example, two MOSFET electronic switches are utilized. Each MOSFET 305 is piloted by a piloting circuit 306, which is fed by the voltage 302 supplied by a direct-voltage rectified feeder of known type (not shown), in which it is possible to adjust the output voltage, which can be also of a switching type, to obtain better efficiency.

The piloting circuit 306 is also adjusted by a current controller 310, which also includes a microprocessor 314.

More exactly, the radiofrequency circuit 30 provides for each MOSFET 305 working as a switch, cutting off the direct current coming from the output 201 of the rectifier circuit 20 and applied to each MOSFET collector.

Each piloting circuit 306 emits a unidirectional square wave 304 of pulsing and non-alternating type, which controls the base of each MOSFET.

The piloting circuit 306 frequency is maintained constant by a quartz oscillator 311, having an oscillation frequency of 4 MHz, connected to a BUFFER 313. The basic oscillation frequency of 4 MHz, and the higher frequencies too, can also be obtained by a circuit or a specific electronic device, such as, for instance, a frequency synthesizer.

The MOSFET 305 piloting is preformed by a signal having an oscillation frequency equal to that of the quartz, or to that of a circuit with similar functions, which is of 4 MHz in the exemplary embodiment.

When the MOSFET 305 is switched off, it cuts the current in branch 301 while, when it is switched on, it allows the passage of current through said branch 301. The waveform amplitude of the current in the branch 301 depends on the control of the signal 302 connected to the piloting circuit 306.

Signal 302 control is performed by a potentiometer 303, or, for example, by a regulator of touch-screen type, allowing selection of the output wave amplitude in order to obtain the power to be supplied to the electrode 41 of the electronic device, according to the interventions to be performed.

To obtain a power adjustment method that is different from the one described in the example, providing for power adjustment by the variation of the feeding voltage 302 of the drivers piloting the power MOSFETS gates, a still direct and rectified (by AC/DC converter or DC/DC converter), but variable, for instance, from 0V to 200V, voltage 201 can be used, while the voltage 302 is maintained steady.

Another possibility is that of using the direct and rectified voltage 201, variable for instance from 0V to 200V, and the variable voltage 302 too to obtain in this case a power adjustment of mixed type.

The output signal of the radiofrequency circuit is thus an impulse current wave 301 at a frequency of 4 MHz, with an amplitude adjusted by the power controller 303, which modifies the voltage 302.

Since the radiofrequency circuit 30 output is connected to the radiofrequency transformer 40 primary, a circulating current 301 is established, which passes through a resonant circuit at the frequency of 4 MHz, where the capacity and the inductance of the resonant circuit are respectively given by the MOSFET's 305 parasitic capacity, by the condenser 30, having negligible reactance but with the function of blocking the direct component of the voltage 201, and by the inductance of the transformer 40 primary circuit.

According to the invention, the resonant circuit is of wide pass-band type, in order to allow the passage, even if attenuated, of at least the second and the third harmonics of the carrier wave related to the signal 301.

Preferably, the signal 301 has at least the second, the third and fourth harmonics.

To obtain a resonant circuit of wide pass-band type, a high frequency transformer was used in the example of FIG. 2, having a number of turns at the secondary circuit that is equal to or greater than the number of turns at the primary circuit.

In this way, the dosage in a decreasing and particular way of the harmonics greater than 4 MHz is obtained, also as a consequence of the kind of intervention to be performed on the skin and/or on the muscle beneath, intervention which changes depending on the different parts to be treated. As known to those of skill in the art, for a resonant circuit the resonance factor Q is given by the formula:

$$Q = \omega C_R R_E = 2\pi f C_R R_E$$

where f is the frequency of resonance, $C_R$ is the capacity of the resonant circuit, $R_E$ is the equivalent Resistance of the primary circuit when the load, consisting, for example, of the body of a patient to be incised with the electronic scalpel, is applied to the secondary circuit.

Since the equivalent Resistance can be expressed with the formula $$R_E = R_C \left(\frac{N_1}{N_2}\right)^2$$

where $R_C$ is the load Resistance and $N_1$ and $N_2$ are the numbers of turns of turns of the primary and the secondary, respectively, it can be easily understood that the resonance factor Q can be expressed with the formula:

$$Q = 2\pi f C_R R_C \left(\frac{N_1}{N_2}\right)^2$$

This formula shows that the resonance factor decreases with an increase of the number of secondary turns with respect to the number of primary turns. The resonance factor can also be expressed with the formula:

$$Q = F_R/B$$

where $F_R$ is the frequency of resonance and B is the pass-band.

In the example of the invention, in order to widen the pass-band of 4 MHz to 8 MHz, 12 MHz and 16 MHz, a transformer with a proper number of turns can be inserted in the resonant circuit, so that the resonance factor is lower than 1, preferably in the range of by 0.6 to 0.7.

With these features of the wide pass-band resonant circuit, the transformer secondary current signal in 401 takes the form as shown in FIG. 3.

Observing the waveform of FIG. 3, it can be noted that at 4, 8, 12 and 16 MHz, there are power peaks that are the interesting ones and which are transferred to the scalpel manipulator with the above-described effects.

It is noted that the current of the signal 401, once set by the power controller 303, is controlled by a current controller belonging to a current sensor 308 placed after the MOSFET 305.

The voltage signal 309, coming from the current sensor 308, controls the current controller 310, which provides for limiting the current 401, by means of fast comparators controlled by the microprocessor 314, acting with the signal 312 on the BUFEER 313 and thus on the MOSFET piloting circuit, or on the supply 201.

The current controller 310 can be a circuit or a specific electronic device, or the same microprocessor 314, which controls the entire system.

The current control can be also performed by the microprocessor 314, which controls the entire system, without employing fast comparators.

In case of low impedance, since the current would reach very high values, a current limiter is present in the circuit, consisting in the inductance 402 which limits the current at the electrodes 41 and avoid exceeding the maximum admissible value on the current in the circuit.

The electric circuit is closed by the resistive load of the person undergoing cosmetic treatment, thus between the electrodes 41, the resistive load of the person and the ground 42.

The upper diagram 3a of FIG. 3 shows the waveform of the available power at the electrodes 41, while the lower diagram 3b shows the spectrum of the basic frequency at 4 MHz and the different harmonics at 8, 12 and 16 MHz. Advantageously, the electrodes 41 have the form of flexible and thin layers, each of them consisting, for example, of an aluminum or copper layer.

Said electrodes are provided with means for skin adhesion in order to allow stable contact between the electrode and the skin during treatment and for subsequent easy removal.

The surface area of each electrode preferably, but not necessarily, ranges from 5 to 15 $cm^2$.

According to the cosmetic method of treating skin and muscle ageing of the invention, said one or more electrodes 41 are applied on the skin of the area to be treated by adhesive means.

The adhesive means can be a bonding agent that is easy to remove from the electrode and especially from the skin, or a suction cup or equivalent means, such as pads fixed both to the skin and the electrodes.

Once the electrodes application is finished, and there is safe and continuous contact between said electrodes and the skin to be treated, the electronic device of the invention is activated so that the waves generated by said device reach the skin surface for a time interval considered optimal in most cases when ranging between 0.5 and 5 minutes. However, it is anticipated that other applications could request longer time intervals.

During said treatment stage, the power employed and dissipated by the electrodes does not exceed a total of 40-50 watts, dissipated by the wide-surfaced electrodes.

It has been noted that, for a good cosmetic treatment, the supplied power in relation to the surface of the electrodes applied on the skin preferably should not be greater than 0.5 $W/cm^2$.

Performed tests have evidenced that, with such a treatment repeated from 5 to 7 times with the same above-described conditions, a considerable reduction of—superficial wrinkles and an increase of muscular tone are achieved, because a regeneration of the tissue beneath the epidermis is achieved, also as a consequence of recovered membrane permeability.

Said tissue, being regenerated, recovers its youthful turgidity and thus the overlying skin is stretched again, with the effect of a considerable reduction in wrinkles and cutaneous relaxation.

The invention claimed is:

1. A cosmetic method of treating skin ageing, comprising the following steps:
   a) connecting a device for treating skin ageing, the device comprising:
      one or more electrodes of essentially laminar shape, to be applied on the skin by adherence and connected to an electronic device, said electronic device comprising:
      a rectifier circuit fed by a power grid voltage which supplies a voltage, to a radiofrequency circuit;
      the radiofrequency circuit comprising at least an electronic switch fed by said voltage and piloted by a piloting circuit, wherein said radiofrequency circuit output consists of a current wave of distorted sinusoidal form by the presence of harmonics of at least the second and third order, said resultant wave circulating in a broadband resonant circuit on the frequency of the pure wave of said distorted sinusoidal form;
   b) applying said one or more electrodes on the skin surface in the area to be treated;
   c) activating said electronic device in order to transfer said current waves to said one or more electrodes and to maintain said device activated for a predetermined time;
   d) deactivating said device and removing the electrodes from the contact with the treated area.

2. The method according to claim 1) wherein said sinusoidal wave is distorted by the presence of harmonics from at least the first to third order.

3. The method according to claim 1) wherein said distorted sinusoidal wave form applied to one or more electrodes has a frequency greater than 2 MHz.

4. The method according to claim 1) wherein the distorted sinusoidal wave applied to one or more electrodes has a frequency of about 4 MHz.

5. The method according to claim 1) wherein the maximum power transmitted to said one or more electrodes is in the range of 40-50 Watts.

6. A device for treating skin ageing, comprising:
   one or more electrodes of essentially laminar shape, to be applied on the skin by adherence and connected to an electronic device, said electronic device comprising:
   a rectifier circuit fed by a power grid voltage which supplies a voltage, to a radiofrequency circuit;
   the radiofrequency circuit comprising at least an electronic switch fed by said voltage and piloted by a piloting circuit, wherein said radiofrequency circuit output consists of a current wave of distorted sinusoidal form by the presence of harmonics of at least the second and third order, said resultant wave circulating in a broadband resonant circuit on the frequency of the pure wave of said distorted sinusoidal form.

7. The device according to claim 6) wherein said resonant circuit comprises at least the parasitic capacity of said electronic switch and the inductance of the radiofrequency transformer primary circuit which feeds said one or more electrodes.

8. The device according to claim 6) wherein said piloting circuit is connected to a controller circuit comprising a microprocessor which interrupts at prefixed intervals the feeding of said piloting circuit, so that the resultant wave which goes through the resonant circuit takes the form of a intermittent pulses train, each of them consisting in an amplitude modulated wave.

9. The device according to claim 6) wherein the wave form amplitude at the electrode is variable by means of a regulator which modifies the voltage of the piloting circuit.

10. The device according to claim 6) wherein the wave form amplitude at the electrode is variable by the modification of the rectified direct voltage which feeds said radiofrequency circuit, being maintained constant the voltage feeding the pilot circuit of said at least an electronic switch.

11. The device according to claim 6) wherein the wave form amplitude at the electrode is variable by the modification of the rectified direct voltage which feeds said radiofrequency circuit and by means of a regulator which modifies the voltage of the piloting circuit.

12. The device according to claim 6) wherein said one or more electrodes of essentially laminar shape comprise an adhesive surface able to be easily applied and removed from the skin.

13. The device according to claim 6), wherein said distorted sinusoidal waveform applied to one or more electrodes has a frequency of about 4 MHz.

14. The device according to claim 6), wherein the ratio between the supplied power to said one or more electrodes and the surface of said electrodes is not greater than 0.5 W/cm$^2$.

15. The device according to claim 6), wherein the broadband resonant circuit is a pass-band circuit.

* * * * *